US012715848B2

(12) United States Patent
Braune et al.

(10) Patent No.: US 12,715,848 B2
(45) Date of Patent: Aug. 25, 2026

(54) PROCESS FOR THE DIASTEREOMERICALLY PURE PREPARATION OF DL/LD-METHIONYLMETHIONINE

(71) Applicant: Evonik Operations GmbH, Essen (DE)

(72) Inventors: Sascha Braune, Dossenheim (DE); Geert Van Eester, Antwerp (BE); Hans-Joachim Hasselbach, Gelnhausen (DE); Claudia Dyballa, Munich (DE)

(73) Assignee: Evonik Operations GmbH, Essen (DE)

( * ) Notice: Subject to any disclaimer, the term of this patent is extended or adjusted under 35 U.S.C. 154(b) by 459 days.

(21) Appl. No.: 18/259,356

(22) PCT Filed: Dec. 23, 2021

(86) PCT No.: PCT/EP2021/087451
§ 371 (c)(1),
(2) Date: Jun. 26, 2023

(87) PCT Pub. No.: WO2022/144292
PCT Pub. Date: Jul. 7, 2022

(65) Prior Publication Data

US 2024/0083858 A1 Mar. 14, 2024

(30) Foreign Application Priority Data

Dec. 30, 2020 (EP) .................................... 20217816

(51) Int. Cl.
*C07D 241/08* (2006.01)
*A23K 20/142* (2016.01)
*A23K 50/80* (2016.01)

(52) U.S. Cl.
CPC .......... *C07D 241/08* (2013.01); *A23K 20/142* (2016.05); *A23K 50/80* (2016.05); *C07B 2200/07* (2013.01)

(58) Field of Classification Search
None
See application file for complete search history.

(56) References Cited

FOREIGN PATENT DOCUMENTS

| | | | | |
|---|---|---|---|---|
| CA | 2740663 | * | 4/2010 | A23K 50/80 |
| CN | 101720858 A | | 6/2010 | |
| CN | 101735125 A | | 6/2010 | |
| CN | 105646304 A | | 6/2016 | |
| DE | 2 261 926 A1 | | 6/1974 | |
| WO | WO 2010/043558 A1 | | 4/2010 | |

OTHER PUBLICATIONS

International Search Report & Written Opinion issued Apr. 28, 2022 in PCT/EP2021/087451 filed on Dec. 23, 2021 18 pages.
European Search report issued Apr. 18, 2021 in EP 20217816.6 filed on Dec. 30, 2020 12 pages (with English Translation of Category of Cited Documents).
Zhang, D. et al. "A facile synthesis of cysteine-based diketopiperazine from thiol-protected precursor", Royal Society open science, (Jun. 1, 2018), XP055799033, 8 pages.
Baker, D.H. et al. "Methionine Peptides as Potential Food Supplements: Efficacy and Susceptibility to Maillard Browning" American Institute of Nutrition, vol. 114, No. 2, 1984, (Jul. 25, 1983), XP002564018, 6 pages.

* cited by examiner

*Primary Examiner* — Craig D Ricci
(74) *Attorney, Agent, or Firm* — Oblon, McClelland, Maier & Neustadt, L.L.P.

(57) ABSTRACT

The invention relates in particular to a process for the preparation of DL/LD-methionine diketopiperazine (I) characterized in that a DD/LL-methionylmethionine-containing aqueous solution or suspension, which has a pH of 3 to 7, measured using a pH electrode at 20° C., is reacted at a temperature of 150 to 220° C., preferably at 170 to 210° C., until an aqueous solution or suspension has formed containing at least a proportion of 30 mol %, preferably 50 mol %, especially 60 mol % of DL/LD-methionine diketopiperazine, based on the total content of DL/LD- and DD/LL-methionine diketopiperazine in the reaction mixture. This process forms part of an overall process for the preparation of DL/LD-methionylmethionine, which is obtained by hydrolysis from the DL/LD-methionine diketopiperazine (I) produced initially.

(I)

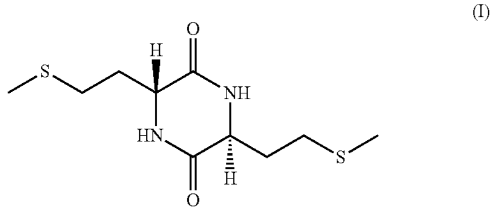

6 Claims, 2 Drawing Sheets

Figure 1: Process scheme for the preparation of DL,LD-methionylmethionine
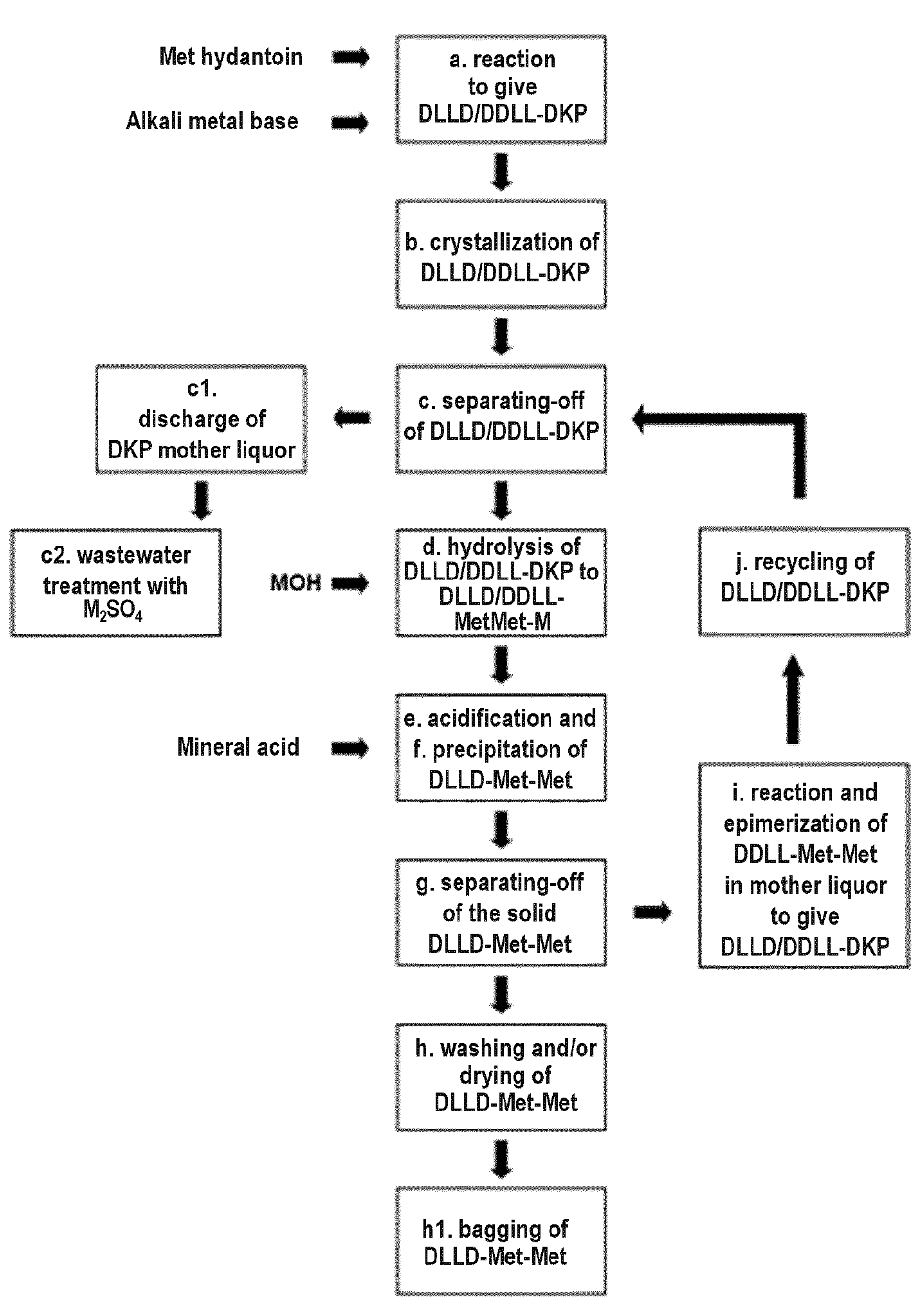

Figure 2: pH as a function of temperature measured in a DD,LL-methionylmethionine-containing solution for the preparation of DL,LD-methionine diketopiperazine
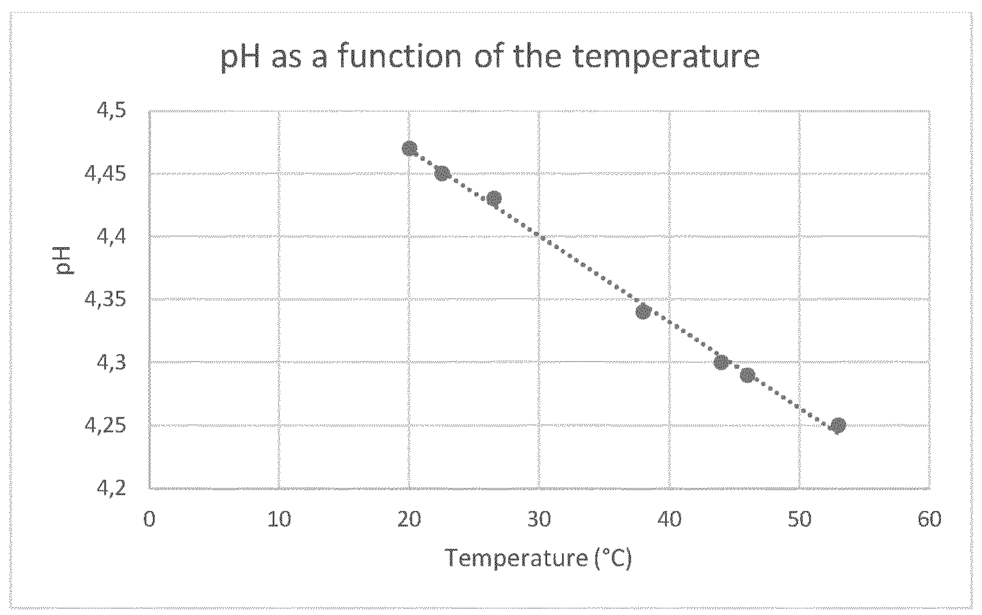

PROCESS FOR THE DIASTEREOMERICALLY PURE PREPARATION OF DL/LD-METHIONYLMETHIONINE

CROSS REFERENCE TO RELATED APPLICATIONS

This application is a National Stage entry under 35 U.S.C. § 371 of PCT/EP2021/087451, filed on Dec. 23, 2021, and claims priority to European Patent Application No. 20217816.6, filed on Dec. 30, 2020, the entire contents of which are incorporated herein by reference.

INTRODUCTION

The present invention relates to a process for the diastereomerically pure preparation of DL/LD-methionylmethionine from DD/LL-methionylmethionine by means of cyclization and epimerization to give DL/LD-2,6-bis (methionyl)-1,4-diketopiperazine (I, meso-methionine-DKP, meso-met-DKP) and subsequent hydrolysis. "Diastereomerically pure" and "essentially diastereomerically pure" are understood in this context to mean a product which contains at least 90 mol % of the desired DL/LD diastereomers, preferably at least 95 to 97 mol % based on the total content of methionylmethionine (Met-Met) present.

(I)

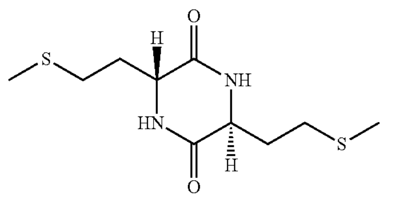

WO2010043558 A1 discloses a process for the preparation of methionylmethionine (Met-Met), the homologous dipeptide of DL-methionine, which increasingly finds use primarily as a high-value methionine source for the feeding of fish and crustaceans kept in aquacultures.

Due to its two stereocentres (two asymmetrical carbon atoms), the product exists in the form of two diastereomers, DL,LD-Met-Met and DD,LL-Met-Met, that is to say in the form of two configurationally isomeric enantiomer pairs, which can both be utilized practically equally well by the animals but which possess markedly different physical properties which in practical handling can lead to certain problems:

It has been found that the two diastereomers form different crystal structures. While DLLD-Met-Met forms a spherical agglomerate in the end product precipitation, DDLL-Met-Met crystallizes out in the form of needles. This is associated with differing flowability and tendency to clumping, and also differing solubility.

While DLLD-Met-Met at room temperature has a water solubility of just 0.4 g/l, the water solubility of DDLL-Met-Met is much higher at 21.0 g/l. However, a high water solubility is rather unfavourable for use in aquacultures since losses of substances of value can arise as a result of leaching from the feed pellet. The product from the preparation process according to WO2010043558 A1 typically has a DLLD-/DDLL-Met-Met ratio of 60/40. A product having a much higher proportion of DLLD-Met-Met would therefore be desirable. In addition, the product known to date exhibits relatively low bulk densities of at most 500 kg/m$^3$, only moderate to relatively poor flowabilities of 3 (satisfactory) to 5 (poor), and a relatively low minimum ignition energy of MIE <3 mJ, and is therefore comparatively highly flammable, and hence these properties also appear to be in need of improvement.

The synthesis of 2,5-diketopiperazine proceeding from methionine methyl ester is already disclosed in publication DE 2 261 926 from 1972. It is disclosed therein that heating of the isopropyl ester of methionine forms 3,6-bis[2-(methylthio)ethyl]-2,5-piperazinedione (methionine diketopiperazine, DKP). The publication by Baker, D. H. et al. (Journal of Nutrition, volume 114, no. 2, 1984, pages 292-297) also relates to this process for preparing diketopiperazine. However, the use of methionine isopropyl ester as starting material is too costly and therefore uneconomic.

Problem

The problem addressed by the underlying invention was therefore that of providing a process for the preparation of a DLLD,DDLL-Met-Met quality which has a much higher proportion of DLLD-Met-Met based on the total amount of diastereomers compared to the prior art product, and also the provision of a product which is intended to additionally have maximally improved handling and safety-related properties compared to the previous product.

DESCRIPTION OF THE INVENTION

The stated problem is solved with the present invention in that virtually only the less soluble enantiomer pair, DLLD-Met-Met, is isolated and the undesired DDLL-Met-Met is back-converted into the direct precursor DKP again and in the process is simultaneously epimerized.

A fundamental part of the solution to the abovementioned problems is thus provided according to the invention by a process for the preparation of DL/LD-methionine diketopiperazine (I)

(I)

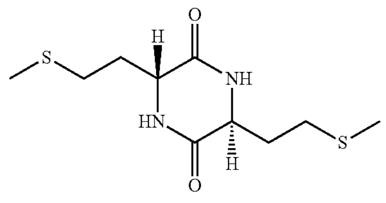

characterized in that a DD/LL-methionylmethionine-containing aqueous solution or suspension, which has a pH of 3 to 7, preferably 4 to 6, especially of approx. 5, measured using a pH electrode at 20° C., is reacted at a temperature of 150 to 220° C., preferably of 170 to 210° C., until an aqueous solution or suspension has formed containing at least a proportion of 30 mol %, preferably 50 mol %, especially 60 mol % of DL/LD-methionine diketopiperazine, based on the total content of DL/LD- and DD/LL-methionine diketopiperazine in the reaction mixture (see Examples 3 to 11). This can then be hydrolysed to give the corresponding methionylmethionine isomer mixture. Higher pH values of >9 or lower pH values of <3 lead to lower yields or less favourable end ratios of DLLD/DDLL-DKP, as shown by Comparative Examples 1 and 2.

In the investigations performed, by way of example, a sodium sulfate-containing, virtually exclusively DDLL-Met-Met-containing mother liquor from the industrial Met-Met process according to WO2010043558 A1 was heated to temperatures above 170° C. and preferably held for approximately one hour. At pH 5, not only was DKP formed quantitatively, but there was also surprisingly simultaneously observed an epimerization of the expected DDLL-DKP (>95%) to give a mixture of DLLD-DKP/DDLL-DKP with a ratio of approximately 60/40 (in particular Example 10). This surprising epimerization of a stereocentre of the DKP forms the basis for, after a solid/liquid separation, being able to feed the DKP obtained in this way back into the existing process for converting DKP to Met-Met. In parallel, a sodium sulfate-containing waste stream is generated as a result, which has a markedly reduced loading of TOC/COD (ratio of total organic carbon to chemical oxygen demand) than to date. The reduction in the TOC/COD loading of the wastewater stream results from the much lower solubility of DKP compared to Met-Met.

Such a process is preferably conducted such that the total concentration of DL/LD- and DD/LL-methionylmethionine equivalents in the form of DL/LD- and DD/LL-methionine diketopiperazine in the reaction mixture at the end of the reaction is in the range from 0.1% to 18% by weight, particularly preferably in the range from 1% to 15% by weight. However, it is simplest and most advantageous to operate at the concentration of approx. 3% by weight which establishes itself in the process, since this can be achieved without additional energy consumption for concentration and despite this a sufficient amount of DKP (and hence TOC) can be isolated from the waste stream.

The reaction is preferably carried out at a temperature of 175 to 210° C. This in turn has the advantage that the reaction is effected in industrially reasonably achievable reaction times. However, a further increase in the temperature beyond this is limited by decomposition at the methylthio group which occurs in parallel.

In addition, in the process according to the invention a DD/LL-methionylmethionine-containing aqueous solution or suspension may be used which already contains DL/LD-methionylmethionine, specifically in approximately up to a proportion of 30 mol % DL/LD-methionylmethionine based on its total content of DD/LL- and DL/LD-methionylmethionine. This is advantageous since, depending on the process conditions, batches may also be obtained which contain somewhat higher proportions of DL/LD-methionylmethionine and which can thus be processed without problems.

The process according to the invention can be operated with residence times of 30 to 120 min, preferably 60 to 90 min. In this case, it is even possible according to Examples 10 and 11 to obtain DKP yields of 96-98% with at the same time a highly favourable DKP end ratio of 60/40 or 53/47 DLLD/DDLL-DKP. This is especially surprising since the prior art process used as comparison (WO 2010/043558 A1, page 45a, Comparative Example 12, Table 1) requires a significantly longer reaction time of 6 h and leads to a poorer result both in terms of DKP yield (51%) and in terms of DKP end ratio DLLD/DDLL-DKP (46/54) (see hereinafter).

In contrast to the present invention, WO 2010/043558 A1 discloses an alternative embodiment of the process according to the invention described there, comprising the following steps:

i) converting a urea derivative of the general formula II, (II)

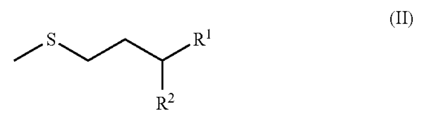

where the radicals R1 and R2 in the urea derivatives IIa, IIb, IIc, IId, IIe, IIf and IIg are defined as follows:

where IIa: $R^1$=COOH, $R^2$=$NHCONH_2$

IIb: $R^1$=$CONH_2$, $R^2$=$NHCONH_2$

IIc: $R^1$=$CONH_2$, $R^2$=$NH_2$

IId: $R^1$—$R^2$=—CONHCONH—

IIe: $R^1$=CN, $R^2$=OH

IIf: $R^1$=CN, $R^2$=$NH_2$

IIg: $R^1$=0, $R^2$=H to give a diketopiperazine of the formula III (III)

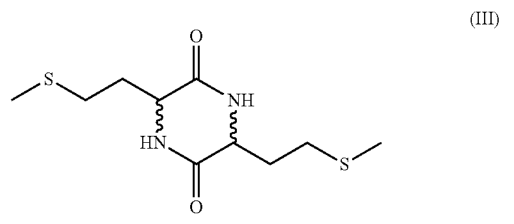

ii) converting the diketopiperazine to DL-methionyl-DL-methionine. This process comprises the methods A, B, C and D shown in scheme 3 of WO2010043558 A1. In these processes, diketopiperazine (III) is formed as intermediate.

It is preferable here for the conversion of the urea derivative to give the diketopiperazine to be conducted at a temperature of 50° C. to 200° C., preferably of 100° C. to 180° C., and particularly preferably of 140° C. to 170° C.

In a preferred process, the urea derivative is converted to the diketopiperazine under pressure, preferably at a pressure of 3 to 20 bar, particularly preferably at a pressure of 6 to 15 bar.

The urea derivative is preferably converted to the diketopiperazine in the presence of a base. In this case the base is preferably selected from the group of nitrogen-containing bases, $NH_4HCO_3$, $(NH_4)_2CO_3$, $KHCO_3$, $K_2CO_3$, $NH_4OH$/$CO_2$ mixture, carbamate salts, alkali metal bases and alkaline earth metal bases.

In a further preferred process, the urea derivative is converted to the diketopiperazine by reaction with methionine. Preference is given here to a ratio of urea derivative to methionine of 1:100 to 1:0.5.

In a further preferred process, the diketopiperazine is converted to DL-methionyl-DL-methionine by acid hydrolysis.

In contrast to the above described process according to WO 2010/043558 A1, the present invention is not aimed at directly converting the less desirable DD,LL-Met-Met diastereomer into the desired DL,LD-Met-Met diastereomer, but instead the crucial step according to the invention of the simultaneous cyclization and epimerization proceeding from the DD,LL-Met-Met diastereomer to the DLLD-DKP mixture is surprisingly accomplished by application of the abovementioned reaction conditions. The DLLD-DKP mixture can then subsequently be hydrolysed to the corresponding DLLD-Met-Met mixture in high yields. The yields in this case are much higher than in the previously cited process according to WO 2010/043558 A1 and are practically devoid of the formation of Met as by-product.

A further subject of the present invention is the following overall process (cf. FIG. 1) for obtaining diastereomerically pure DL/LD-methionylmethionine, characterized in that a. methionine hydantoin together with alkali metal base is converted to afford a diastereomeric mixture of DL/LD-methionine diketopiperazine and DD/LL-methionine diketopiperazine (DLLD-DKP and DDLL-DKP)
b. the DLLD-DKP and DDLL-DKP from a. are brought to crystallization by concentrating or cooling the reaction solution from a.
c. the DLLD-DKP and DDLL-DKP crystallized out are separated off from the DKP mother liquor
d. the DLLD-DKP and DDLL-DKP separated off are mixed into water and the mixture is brought, by addition of appropriate amounts of MOH (M=alkali metal), to a pH of 10 to 14, preferably 13, measured using a pH electrode at 20° C., and is hydrolysed at a temperature of from 90 to 150° C. with a residence time of 30 to 180 min to give a corresponding aqueous solution or suspension of a diastereomeric mixture of DL/LD-methionylmethionine alkali metal salt and DD/LL-methionylmethionine alkali metal salt,
e. the pH of the solution or suspension from d., measured at 20° C., is lowered by addition of appropriate amounts of acid to ≤7, preferably to 4 to 6, particularly preferably to 4.7 to 6.0 (acidification),
f. evaporation of water and/or cooling is/are used to produce a suspension (precipitation) which consists of a solids fraction, which predominantly contains DL/LD-methionylmethionine, and mother liquor, which predominantly contains DD/LL-methionylmethionine,
g. the solids fraction from f. is separated off from the mother liquor and
h. the solids fraction separated off from g. is alternatively washed and/or dried, with diastereomerically pure DL/LD-methionylmethionine being obtained, and
i. the remaining DD/LL-methionylmethionine-containing mother liquor from g. is reacted according to the procedure described above (cf. also Claim 1) so that an aqueous solution or suspension containing a diastereomeric mixture of DL/LD-methionine diketopiperazine and DD/LL-methionine diketopiperazine is formed having a proportion of up to 60 mol % DL/LD-methionine diketopiperazine based on the total content of DL/LD- and DD/LL-methionylmethionine equivalents in the reaction mixture and
j. this is then recycled into step b.

The separation of the diastereomeric enantiomer pairs can be achieved by fractional crystallization at temperatures above 50° C. and Met-Met concentrations below 15%, preferably below 10%. Under these conditions, virtually exclusively the enantiomer pair of DLLD-Met-Met can be selectively precipitated. The DDLL-Met-Met remains in solution to an extent of over 95%. Such a separation is not possible with the starting product, the cyclic dipeptide DKP, which has a ratio of DLLD-DKP/DDLL-DKP of 55/45.

In step d. preferably 0.9 to 1.5 molar equivalents, particularly preferably 1.0 to 1.2 molar equivalents, of base are used based on the total content of DL/LD- and DD/LL-methionylmethionine equivalents in the reaction mixture. This procedure brings about virtually quantitative hydrolysis of the DKP precursor to the dipeptide.

As base used in step d., preference is given to alkali metal hydroxides, particularly preferably NaOH or KOH, since these have a sufficiently high alkalinity and solubility, and are industrial chemicals that are relatively inexpensive and at the same time available in high quality and additionally are entirely unproblematic with respect to any traces possibly remaining in the end product.

As acid used in step e., preference is given to strong mineral acids, such as for example phosphoric acid, hydrochloric acid or sulfuric acid, especially sulfuric acid. When neutralized with NaOH or KOH, sulfuric acid forms the corresponding sodium or potassium sulfates, which have proved to be particularly helpful in separating off the product DL/LD-methionylmethionine, since particularly well filterable product crystals are formed in particular in the event of prior use of NaOH.

In step f. cooling is preferably effected down to a temperature of >50° C. This has the effect that at most small proportions of DDLL-Met-Met that are still present also precipitate out, meaning that in the product only a proportion of less than 5% of the undesirable diastereomer DDLL-Met-Met still remains.

The process is preferably conducted such that the suspension produced in step f. contains at least 1% by weight, but not more than 15% by weight, total content of DD/LL- and DL/LD-methionylmethionine. In this way it is achieved that relatively well filterable crystals, predominantly consisting of DLLD-Met-Met, can be produced.

The separation of the enantiomer pairs can therefore advantageously be achieved by fractional crystallization at temperatures above 50° C. and at Met-Met concentrations below 10%. Under these conditions, virtually exclusively the enantiomer pair of DLLD-Met-Met can be selectively precipitated. The DDLL-Met-Met remains in solution to an extent of over 95%. As already stated, such a separation is not possible with the starting product, the cyclic dipeptide DKP, which has a ratio of DLLD-DKP/DDLL-DKP of approx. 55/45.

The solids fraction separated off in step g. is further purified and/or dried, resulting in the obtaining of a pulverulent, substantially diastereomerically pure DL/LD-methionylmethionine which is directly suitable for use as an animal feed additive for aquacultures.

The invention therefore further provides a pulverulent, substantially diastereomerically pure DL/LD-methionylmethionine, obtainable by one of the above described processes of the invention, which is suitable for use as an animal feed additive for aquacultures.

Such a pulverulent, substantially diastereomerically pure DL/LD-methionylmethionine-containing product has the following features:

a. at least 97% by weight total content of DD/LL- and DL/LD-methionylmethionine,
b. at least 90 mol % DL/LD-methionylmethionine and at most 10 mol % DD/LL-methionylmethionine, preferably at least 95 mol % DL/LD-methionylmethionine and at most 5 mol % DD/LL-methionylmethionine, based in each case on the total content of DD/LL- and DL/LD-methionylmethionine,
c. at most 1.0% by weight residual moisture,
d. at most 2.0% by weight sulfate (ash) and
e. a particle size distribution with a median D50 of 80 to 300 μm, preferably 150 to 250 μm.

The product is suitable in particular for use as an animal feed additive for aquacultures since it is relatively poorly soluble in water and hence can hardly be lost as a result of leaching from a feed pellet into which it has been incorporated beforehand.

The invention accordingly further provides for the corresponding use of substantially diastereomerically pure DL/LD-methionylmethionine as an animal feed additive for aquacultures. After a solid/liquid separation and drying, highly pure AQUAVI®Met-Met is obtained with a diastereomeric ratio of ≥95/≤5 DLLD/DDLL-Met-Met. This novel product has bulk densities of significantly above 600 $kg/m^3$ compared to the prior DLLD/DDLL-Met-Met product mixture, the standard product from WO2010043558 A1, at only less than 500 $kg/m^3$. The novel product also exhibits markedly improved flow characteristics, generally of flow grade 3 or better (satisfactory to good) on the scale from 1 to 6 measured with standard orifice cylinders (cf. examples Analytical Methods) compared to the prior DLLD/DDLL-Met-Met product mixture, which generally has a flow grade of 5 to 6. In addition, the minimum ignition energy of the product according to the invention at room temperature is above 10 mJ and even at 100° C. is still above 3 mJ, and can therefore no longer be classified as particularly sensitive to ignition. This is highly advantageous for safe handling of the product and for the expenses to be incurred therefor.

FIG. 1 shows the scheme for the preparation of DL/LD-methionylmethionine

The scheme comprises the following steps:

a. reaction of methionine hydantoin with alkali metal base to give DLLD/DDLL-Met-DKP
b. crystallization of DLLD/DDLL-Met-DKP
c. separating-off of DLLD/DDLL-Met-DKP
   c1. discharge of DKP mother liquor
   c2. wastewater treatment
d. alkaline hydrolysis of DLLD/DDLL-Met-DKP to DLLD/DDLL-Met-Met
e. acidification and
f. precipitation of DLLD-Met-Met
g. separating-off of the solid DLLD-Met-Met
h. washing and/or drying of DLLD-Met-Met
   h1. bagging of DLLD-Met-Met
i. reaction and epimerization of DDLL-Met in DDLL-Met-containing mother liquor to give DLLD/DDLL-Met-DKP
j. recycling of DLLD/DDLL-Met-DKP into step c.

FIG. 2 shows pH as a function of temperature measured in a DDLL-methionylmethionine-containing solution for the preparation of DL,LD-methionine diketopiperazine, said solution having a content of 3% by weight of DD,LL-methionylmethionine and being used thus in Industrial Example 10. This solution did not contain any $KHCO_3$, in contrast to Comparative Example 12 which was conducted in accordance with WO 2010043558 A1, page 45a). Dispensing with a further additive ($KHCO_3$) is additionally a great advantage with respect to the process from the WO document.

EXAMPLES

Unless otherwise stated, the examples were performed as per the general process description and in accordance with the respectively associated information in Table 1.

Analytical Methods

Determination of Bulk Density

The bulk density in kg/L was determined using a 1 L measuring cylinder, which was filled with the bulk material precisely to the 1000 ml mark, and was measured by weighing the weight of the contents so as to result in the bulk density directly.

Determination of Flow Characteristics

The flow characteristics (flowability) was determined by assigning a flow grade of 1 (very good) to 6 (unsatisfactory) on the basis of prior measurement of the flowability using standard glass orifice vessels. These had a cylindrical shape with a conical lower end in the centre of which an orifice was positioned (analogous to a silo) of differing width ranging from narrow for grade 1 to relatively wide for grade 6. The measurement was started with the narrowest orifice vessel, the orifice was kept closed with a glass plate, the orifice vessel was filled with the bulk material, the glass plate was removed and the outflow was assessed. Only when a virtually uninhibited outflow of the bulk material could be observed was a grade of 1 given. If this was not the case, the next-wider orifice vessel was used and a grade of 2 was assigned in the event of flawless outflow; if this was not the case once again, the next-wider orifice vessel was used, and so on up to the widest orifice vessel (vessel 5). Only material which could not flow uninhibited from this orifice vessel either was assessed with a grade of 6. The standard orifice vessels all had a height of the cylindrical portion of 70 mm and an internal width of 36 mm. The orifices had the following widths for vessel 1: 2.5 mm, vessel 2: 5 mm, vessel 3: 8 mm, vessel 4: 12 mm, vessel 5: 18 mm.

Determination of pH

Unless otherwise indicated, the pH was measured with a glass electrode in aqueous solution and at a temperature of 20° C.

The quantitative determination of the concentrations of Met, Met-Met, methionyl-DKP and so on was effected using standard HPLC methods against an external standard.

General Process Description of the DKP Synthesis

An aqueous solution of the dipeptide Met-Met, after adjusting the pH to 4.5 or 5 using either sulfuric acid or caustic soda, was heated to 150-180° C. for a period of 30-120 min. After cooling to 70° C. by reducing the pressure, an aqueous suspension was obtained. After filtering off and washing the filter cake with water, a solid was obtained which primarily contained DKP which consisted of a mixture of DLLD-DKP and DDLL-DKP in a ratio in the most favourable case of 50/50 or greater, independently of the stereochemical configuration of the starting material Met-Met.

Example 1 (Variation of pH—Basic Conditions, Comparative Example)

By adjusting the pH to 9.3 and otherwise proceeding according to the general process description, primarily methionine was already formed at temperatures of 140° C. DKP was only obtained in a yield of 34% and with a diastereomeric ratio of 57/43 DLLD/DDLL-DKP, starting from a diastereomeric ratio of 36/64 DLLD/DDLL-Met-Met in the starting material.

Example 2 (Variation of pH—Acidic Conditions, Comparative Example)

By adjusting the pH to 2.9 and otherwise proceeding according to the general process description, primarily methionine was already formed at temperatures of 140° C. DKP was only obtained in a yield of 60% and with a diastereomeric ratio of 36/64 DLLD/DDLL-DKP, starting from the same diastereomeric ratio of 36/64 DLLD/DDLL-Met-Met in the starting material.

Examples 3 to 5 (Variation of Temperature, Reaction Time and pH)

Example 3

Heating the mixture to 150° C., holding at this temperature for 120 min and then holding at 120° C. and pH 9.0 for 60 min and otherwise proceeding according to the general process description afforded DKP in 53% yield with significant epimerization. The ratio of the diastereomers shifted from 15/85 DLLD/DDLL-Met-Met to 60/40 DLLD/DDLL-DKP.

Example 4

In contrast, heating the mixture to 150° C., holding at this temperature for 120 min and pH 4.8 and otherwise proceeding according to the general process description afforded DKP in 80% yield with markedly less epimerization. The ratio of the diastereomers shifted from 15/85 DLLD/DDLL-Met-Met to 25/75 DLLD/DDLL-DKP.

Example 5

In contrast, heating the mixture to 160° C., holding at this temperature for 60 min and otherwise proceeding according to the general process description afforded DKP in 72% yield with significant epimerization. The ratio of the diastereomers shifted from 15/85 DLLD/DDLL-Met-Met to 39/61 DLLD-/DDLL-DKP.

Example 6

1.47 kg of an aqueous solution having a content of 2.9% DDLL-Met-Met (151 mmol) and 0.9% DLLD-Met-Met (50 mmol) were adjusted to pH 4.5 by addition of 10% NaOH. The solution was then heated to a temperature of 170° C. (7 barg) as rapidly as possible and held at this temperature for 90 min. Once Met-Met could no longer be detected analytically, the reaction mixture was cooled down to 100° C. by decompression. The suspension thus obtained was cooled down further to 70° C. under vacuum. Filtering off the solid precipitate formed and washing the filter cake with 150 g of water afforded 98 g of brownish crystals. 43 g of a DKP mixture (161 mmol, 80% yield) composed of both diastereomers was isolated after drying in a ratio of DLLD-/DDLL-DKP of 48/52 with a chemical purity of 98%.

Examples 7 and 8 (Variation of the Reaction Time)

Shortening the reaction time to 60 min and otherwise proceeding according to the process description under Example 6 afforded a lower yield of 73% DKP with a diastereomeric ratio of 52/48 DLLD/DDLL-DKP, and with a 30 min reaction time afforded a yield of 71% with a diastereomeric ratio of 48/52.

Example 9 (Increasing the Reaction Temperature)

A further increase of the temperature to 175° C., holding for 30 min at this temperature and pH 4.5 and otherwise proceeding according to the process description under Example 6 again achieved a somewhat higher yield of 77% DKP compared to Example 8 with a diastereomeric ratio of 38/62 DLLD-/DDLL-DKP.

Example 10 (Reaction Temperature 1750 at pH 6.0)

Analogously to Example 6, an aqueous solution having a content of 2.7% Met-Met and a Met-Met starting ratio DLLD/DDLL of 12/88 and having a pH of 6.0 (Met-Met mother liquor from industrial production plant) was heated as rapidly as possible to a temperature of 175° C. and held at this temperature for 90 minutes. The procedure was otherwise as per the process description under Example 6. An even higher yield of 96% DKP was achieved and at the same time a highly favourable diastereomeric ratio of approx. 60/40 DLLD-/DDLL-DKP.

Example 11 (Reaction Temperature 1750 at pH 4.7)

Analogously to Example 10, an aqueous solution having a content of 3.3% Met-Met and a Met-Met starting ratio DLLD/DDLL of 25/75 and having a pH of 4.7 (Met-Met mother liquor from industrial production plant) was heated as rapidly as possible to a temperature of 175° C. and held at this temperature for 90 minutes. The procedure was otherwise as per the process description under Example 6. An even higher yield of 98% DKP was achieved and at the same time a highly favourable diastereomeric ratio of approx. 53/47 DLLD-/DDLL-DKP.

Example 12 (Variation of the pH, Comparative Example According to WO2010043558 A1, Page 45a))

"Racemization of DL/LD-Methionylmethionine"

12.6 g (45.0 mmol) of DD/LL-methionylmethionine (Met-Met starting ratio DLLD/DDLL of 0/100) were dissolved, together with 4.5 g (45.0 mmol) of $KHCO_3$, in 75 ml of water in a 200 ml Roth laboratory reactor and heated to 160° C. with stirring. The pressure rose to 7 bar, and after 6 hours at this temperature the autoclave was cooled in an ice bath to 20° C. and the pH was determined in the obtained suspension to be pH=9.1 using a glass electrode. The suspension was then filtered, the solid filtered off was washed multiple times with water and dried at 50° C. under reduced pressure in a drying cabinet. The yield isolated was 6.0 g (22.9 mmol) (51%) of bis[2-(methylthio)ethyl]-2,5-piperazinedione (Ill), yellowish-white crystals, purity >98% (HPLC), melting point 233-236° C.; diastereomeric ratio: 54:46 (DD/LL-III:meso-III). The washing water and the mother liquor were combined and concentrated to a volume of 25 ml on a rotary evaporator at 40° C. A moderate $CO_2$ stream was then introduced into the solution obtained until a pH of 6.0 was achieved and a white solid precipitated out. This solid was filtered off, washed with a little cold water, and dried overnight in a vacuum drying cabinet at 50° C. The yield isolated was 5.5 g (19.6 mmol) (44%) of DD/LL/DL/LD-methionylmethionine (I), white solid, purity >98% (HPLC).

Example 13 (Hydrolysis of DLLD/DDLL-Met-DKP to DLLD/DDLL-Met-Met Etc.)

The diastereomeric mixtures of DLLD/DDLL-Met-DKP produced according to Examples 10 and 11 could be hydrolysed according to steps e. to h. (see above and FIG. 1) to the corresponding mixtures of DLLD/DDLL-Met-Met alkali metal salts. After appropriate acidification with, for example, sulfuric acid to pH 4.5 to 5.6, DLLD-Met-Met was precipitated as solid, filtered off, washed and dried. The DLLD-Met-Met thus obtained consistently exhibited flow grades of 1 to 2, bulk densities of >600 kg/$m^3$, and low dust contents of approx. 10% <63 μm. The minimum ignition energies found for these products were above 10 mJ at room temperature and even at 100° C. were still above 3 mJ.

The mother liquor from the filtration, with the DDLL-Met-Met remaining in solution, could then be supplied to step i. of cyclization and epimerization.

TABLE 1

Overview of the examples

| Example | Starting material/ type of reaction | Reaction time [min] | Temp. [° C.] | pH | Met-Met conc. [% by wt.] | DKP Yield [%] | Met-Met starting ratio DLLD/ DDLL | DKP end ratio DLLD/ DDLL |
|---|---|---|---|---|---|---|---|---|
| 1 (comparison) | Met-Met mother liquor/epimerization under basic conditions | 120 | 140 | 9.3 | 10.5 | 34 | 36/64 | 57/43 |
| 2 (comparison) | Met-Met mother liquor/epimerization under acidic conditions | 120 | 140 | 2.9 | 8.9 | 60 | 36/64 | 36/64 |
| 3 | Met-Met mother liquor/cyclization and epimerization at IP (isoelectric point), followed by basic conditions | 120<br>60 | 150<br>120 | 4.5<br>9.0 | 3.4 | 53 | 15/85 | 60/40 |
| 4 | Met-Met mother liquor/epimerization at IP | 120 | 150 | 4.8 | 3.4 | 80 | 15/85 | 25/75 |
| 5 | Met-Met mother liquor/epimerization at IP | 60 | 160 | 4.5 | 3.4 | 72 | 15/85 | 39/61 |
| 6 | Met-Met mother liquor/epimerization at IP | 90 | 170 | 4.5 | 3.4 | 81 | 15/85 | 48/52 |
| 7 | Met-Met mother liquor/epimerization at IP | 60 | 170 | 4.5 | 3.4 | 73 | 15/85 | 52/48 |
| 8 | Met-Met mother liquor/epimerization at IP | 30 | 170 | 4.5 | 3.4 | 71 | 15/85 | 48/52 |
| 9 | Met-Met mother liquor/epimerization at IP | 30 | 175 | 4.5 | 3.4 | 77 | 15/85 | 38/62 |
| 10 | Met-Met mother liquor/production epimerization at pH 6.0 | 90 | 174 | 6.0 | 2.7 | 96 | 12/88 | 60/40 |
| 11 | Met-Met mother liquor/production epimerization at pH 4.7 | 90 | 174 | 4.7 | 3.3 | 98 | 25/75 | 53/47 |
| 12 | Comparative example according to WO2010043558 A1, page 45a), Mixture of DDLL-Met-Met, $KHCO_3$ and $H_2O$ | 360 | 160 | 9.1 | 13.7 | 51 | 0/100 | 46/54 |

The invention claimed is:

1. A process for the preparation of DL/LD-methionine diketopiperazine represented by formula (I):

(I)

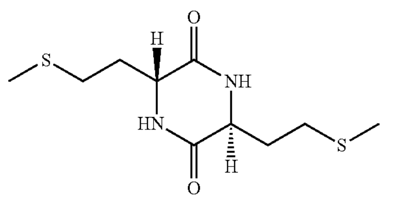

the process comprising:

reacting a DD/LL-methionylmethionine-containing aqueous solution or suspension at a temperature of 170° C. to 210° C. for 30 to 120 minutes to form an aqueous solution or suspension containing at least 50 mol % of DL/LD-methionine diketopiperazine based on the total content of DL/LD- and DD/LL-methionine diketopiperazine in the reaction mixture;

wherein the DD/LL-methionylmethionine-containing aqueous solution or suspension has a pH of 4 to 7 as measured using a pH electrode at 20° C.

2. The process according to claim 1, wherein the DD/LL-methionylmethionine-containing aqueous solution or suspension has a pH of 4 to 6 as measured using a pH electrode at 20° C.

3. The process according to claim 1, wherein the reacting is at a temperature of 175 to 210° C.

4. The process according to claim 1, wherein the total concentration of DL/LD- and DD/LL-methionylmethionine equivalents in the form of DL/LD- and DD/LL-methionine diketopiperazine in the reaction mixture at the end of the reaction is in the range from 0.1% to 18% by weight.

5. The process according to claim 1, wherein the DD/LL-methionylmethionine-containing aqueous solution or suspension further comprises DL/LD-methionylmethionine.

6. The process according to claim 5, wherein the proportion of DL/LD-methionylmethionine in the DD/LL-methionylmethionine-containing aqueous solution or suspension is up to 30 mol % based on the total content of DD/LL- and DL/LD-methionylmethionine.

* * * * *